(12) United States Patent
Haas et al.

(10) Patent No.: US 8,088,332 B2
(45) Date of Patent: Jan. 3, 2012

(54) EXPLOSIVE OR DRUG DETECTION SYSTEM FOR SHIPPING CONTAINERS

(75) Inventors: Jeffrey Haas, San Ramon, CA (US); Doug Haas, Lancaster, CA (US)

(73) Assignee: Chem Spectra, Inc., Lancaster, CA (US)

( * ) Notice: Subject to any disclaimer, the term of this patent is extended or adjusted under 35 U.S.C. 154(b) by 177 days.

(21) Appl. No.: 12/431,604

(22) Filed: Apr. 28, 2009

(65) Prior Publication Data

US 2010/0272609 A1   Oct. 28, 2010

(51) Int. Cl.
*G01N 33/00*   (2006.01)
(52) U.S. Cl. ........ 422/68.1; 422/400; 422/402; 422/403
(58) Field of Classification Search ................. 422/68.1, 422/400, 402, 403
See application file for complete search history.

(56) References Cited

U.S. PATENT DOCUMENTS

| 5,109,691 | A | 5/1992 | Corrigan |
| 5,296,380 | A | 3/1994 | Margalit |
| 5,455,606 | A | 10/1995 | Keeling |
| 5,644,341 | A | 7/1997 | Fujii |
| 5,648,047 | A | 7/1997 | Kardish |
| 5,925,732 | A * | 7/1999 | Ecker et al. ............ 506/40 |
| 7,368,292 | B2 | 5/2008 | Hummel |
| 7,605,367 | B2 | 10/2009 | Miller |
| 7,666,684 | B2 | 2/2010 | Swager |
| 2005/0101027 | A1 | 5/2005 | Haas |
| 2009/0246881 | A1 * | 10/2009 | Toal et al. ............ 436/110 |

OTHER PUBLICATIONS

Manual for ChemSpectra EX-DETECTTM, MINI XD-2, Oct. 2009.
Manual for KeTech Spectrex SPX 300 Trace Explosives Detector, Date Unknown.
Manual for Spectrex EX—Detect TM, Model XD-2 Explosives Detector, Mar. 2007.

* cited by examiner

*Primary Examiner* — Sam P Siefke
(74) *Attorney, Agent, or Firm* — Tran & Associates

(57) ABSTRACT

A tester to detect the presence of a target substance includes a housing that can be mounted on a shipping container; a chemical reservoir insertable into the housing; a disc or an automated cartridge containing test filter swipes adapted to receive particles or vapor, and a chemical from the chemical reservoir, the test swipe including one or more chemically treated pads; a camera to capture an image from the test swipe; a processor coupled to the camera to process the image to detect the target substance; and a transmitter coupled to the processor to transmit a test result to a remote computer.

20 Claims, 6 Drawing Sheets

EXPLOSIVE OR DRUG DETECTION SYSTEM FOR SHIPPING CONTAINERS

BACKGROUND

This invention relates to systems for the detection of explosives and other controlled substances such as drugs or narcotics as well as other chemicals used in clandestine activities.

Recent terror attacks have changed the dynamics of the explosive detection systems across the globe. Terrorists, acting singly or in concert, instill immense fear and apprehension in civilians and governments alike with their technical knowledge about explosives. In parallel, the world has experienced an increase in the transportation of contraband substances such as drugs or narcotics.

As noted in United States Application US20080129493, cargo transit (such as air, ocean, or land transportation) transports containers, vessels, and people. Certain containers, vessels, and/or people may pose safety and security threats. For example, a container may be diverted from a planned route, during which cargo may be exchanged for harmful substances, such as weapons of mass destruction (WMD). In another example, contraband or illegal substances may be hidden inside a container to avoid detection by a authorities. Such safety and security threats should be minimized. One way to minimize potential threats is by restricting containers that have a high probability of threat to areas outside an intended target, protected area, or sensitive environment. The relevant public safety authorities prefer to receive information regarding cargo before the cargo reaches its intended destination. Any necessary exclusion of harmful materials or people should take place before the cargo reaches an intended target.

U.S. patent application No. Ser. 20080129493 discloses a method and apparatus for using a sensor array that detects environmental changes in or around a shipping container. Sensors detect materials and detect tampering with the container (such as broken seals and open doors). The sensors are monitored remotely. The sensors are tracked for determining risk levels and communicating the risks to receiving ports, customs officials, shipping companies, and other interested entities. The sensors can also detect environmental conditions that may be important to the protection of cargo that may not be security-sensitive, but may require special conditions (such as perishable food). The system may categorize cargo into various levels of risk (such as mandatory inspection, occasional inspection, and random inspection). However, this system does not address the detection of explosives or drugs hidden in the container.

SUMMARY

In one aspect, a tester to detect the presence of a target substance includes a housing that can be mounted on a shipping container; a chemical reservoir insertable into the housing; a test swipe adapted to receive a chemical from the chemical reservoir, a test swipe adapted to perform as a filter to collect sample particles, the test swipe including one or more chemically treated pads; a disc, holder or cartridge containing one or more of the test swipes automatically positioning said swipes for sampling and automated analysis, a camera to capture an image from the test swipe; a processor coupled to the camera to process the image to detect the target substance; and a transmitter coupled to the processor to transmit a test result to a remote computer.

Implementations of the above aspect may include one or more of the following. The chemically treated pad can be a substantially round shape. A sequence of one or more chemicals can be delivered to the pad to detect an explosive compound. Each chemical causes the pad to display a color unique to the explosive compound. The sequence of chemicals are deposited onto the pad at predetermined times. The sequence of chemicals is deposited onto the pad at predetermined temperature range(s). The sequence of chemicals is deposited onto the pad at predetermined hold time(s) each at predetermined temperature range(s). Each chemical deposited under predetermined time and temperature conditions reacts to a specific explosive or class of explosives to yield a specific color unique to that explosive. The color is interpreted by the algorithms at specific times, temperature and chemistry to identify or characterize the explosive or class of explosives. The chemically treated pad can be a substantially round shape and adapted to receive a sequence of one or more chemicals to detect an explosive compound. The base can have a dull black color. The pad region can be a cloth with an ink free border.

The chemically treated pad can also be a substantially four-sided shape. One or more chemicals can be deposited onto their respective pads to detect one or more drug compounds. Each chemical causes the pad to display a color unique to the explosive compound. The sequence of chemicals are deposited onto their respective pads at predetermined times. The sequence of chemicals is deposited onto the pad at predetermined temperature range(s). The sequence of chemicals is deposited onto the pad at predetermined hold time(s) each at predetermined temperature range(s). Each chemical deposited under predetermined time and temperature conditions reacts to a specific explosive or class of explosives to yield a specific color unique to that explosive. The chemically treated pad can be a substantially four-sided shape and adapted to receive a sequence of one or more chemicals to detect a drug compound. The chemically treated area can have a plurality of test regions. A plurality of unique chemical solutions can be deposited on each test region generating a unique color of the respective pad. The pads collectively generate a unique color pattern or code for a particular drug or class of drugs. The chemical solutions can be deposited separately or at same time to the respective test regions on the swipe. The base can have a dull black color. The pad region can be a cloth positioned on a zone of the base that is white in color an inert ink free border.

In another aspect, a method to analyze a swiped sample to identify a chemical composition, includes clamping a test swipe under a camera and above a heater, the test swipe having a base; a chemically treated pad containing the swiped sample positioned above the base; and a tab attached to one side of the base; actuating a piezoelectric transducer that deposits a series of chemical solution agents into the swiped sample without dripping so that the device may be held at any angle of position or orientation; heating the swiped sample to one or more predetermined temperatures at a controlled rate and hold times to optimize and accelerate the chemical reactions; capturing one or more images of the chemical reaction; sending the images to the a display screen for operator observation; and analyzing the images to identify the chemical composition based on a chemical reaction and sequence of occurrence and database.

In another aspect, a system is disclosed to remotely and automatically collect sample particles by air filtration on a series of swipes at under remote control or any pre-set, predetermined time. The system can analyze any or all swipes on command to identify a chemical composition collected according to date and time. In one embodiment, the system includes a series of pre-loaded swipes in a cartridge whereby the test swipes are clamped in the holder, rotated in and out of a air filtration position for any period of time controlled by the operator, and the test swipes may then be rotated under a camera and above a heater. The test swipe can have a base; a chemically treated pad containing the swiped sample positioned above the base; and a tab attached to one side of the base. The system can actuate a piezoelectric transducer or pumps that deposits a series of chemical solution agents into the swiped sample without dripping so that the device may be held at any angle of position or orientation; heating the swiped sample to one or more predetermined temperatures at a controlled rate and hold times to optimize and accelerate the chemical reactions. The system then captures one or more images of the chemical reaction; sends the images to the a display screen for operator observation; and analyzes the images to identify the chemical composition based on a chemical reaction and sequence of occurrence and database.

In yet another aspect, a portable handheld chemical analytical apparatus that analyzes a test swipe for chemicals such as household, drug, and clandestine, and explosive chemicals is disclosed. The apparatus includes a heater to warm the test swipe to a predetermined temperature; a clamp to secure the test swipe to the heater; one or more piezoelectric actuators connected to a chemical reservoir to dispense one or more chemicals onto the test swipe; a fan to circulate chemical vapors rising from the test swipe; and a camera to capture an image of the test swipe for analysis.

In another aspect, a method to analyze a swiped sample to identify a chemical composition, includes dispensing a series of chemical solution agents into the swiped sample; heating the swiped sample to one or more predetermined temperatures at a controlled rate to accelerate and optimize the chemical reactions or a series of chemical reactions reproducibly; capturing one or more images of the chemical reaction; sending the images to the display screen for operator observation; and analyzing the images electronically to identify the chemical composition in an unbiased fashion based on a chemical reaction database.

Advantages of the system may include one or more of the following. The system can determine quickly and reliably dangerous containers. The system tests the presence of chemical materials or compounds using a number of factors or parameters singly or in concert. The factors can include heat, volume, time, temperature, and vapor control, among others and sequences these factors over time. The sequences can be in unique intervals. As a result, the system produces highly reliable color results from specific reaction chemistry under the controlled parameters and reduces "false positives" due to its multi-factor, multi-step diagnostic operations.

The device is accurate, can operate in any orientation, requires low power, and is small in size. The device significantly enhances the possibility of also being applied to accurately and quickly screen personnel, equipment, and materials at security checkpoints, military operations, law enforcement, or other screening scenarios, and for detecting trace explosive materials, night or day, very high humidity and bad-weather conditions. The system allows users to precisely and quickly detect different explosive chemical threat agents.

The system operates in a real-time fashion. It automatically and remotely collects samples and then dispenses a precise volume of chemical solutions over time when requested. The system optionally allows users to manually control the sequence of the pumping process. The system provides users with pump controls for dispensing chemical solutions. Through the built-in heater, the system automatically heats up the swiped sample to predetermined temperatures over specific time parameters using an automatic ramped heating feedback control. The system automatically and continually performs self-check and monitors fluid levels, temperature and time. The system automatically chronologically analyzes and stores data and arranges according to positive results versus negative results. The system automatically tells the operator to remove the analyzed swipe. The system delivers a unique sequence of precise chemical volumes under time, heat, and vapor parameters. The system has detachable and expendable chemical(s) in cartridge form for ease of replacement. The system uses a high-resolution digital camera for data collection and un-biased automated analysis.

By use of a wired or wireless transceiver, detected information can be easily transmitted to anywhere in the world. By replacing disposable swipes/pads/swabs and disposable chemical test reservoirs, the system can detect a wide range of explosives, clandestine material, drugs, and household products used to manufacture explosives, a range of controlled chemical agents, drugs, and narcotics etc. By allowing the user to swipe test materials and running computerized diagnostics, the user can easily and effectively change the system to meet what is considered to be the threat at that time. By having all components under program control and by arranging for a known input to the system such as a controlled injection of target material, the system can perform self-calibration and self-diagnostics.

BRIEF DESCRIPTION OF THE DRAWINGS

The above and other objects, features, and advantages of the present invention will be better understood from the following detailed descriptions taken in conjunction with the accompanying drawings, all of which are given by way of illustration only, and are not limitative of the present invention, in which.

DESCRIPTION

The following detailed description of the invention is provided to aid those skilled in the art in practicing the present invention. Even so, the following detailed description of the invention should not be construed to unduly limit the present invention, as modifications and variations in the embodiments herein discussed may be made by those of ordinary skill in the art without departing from the spirit or scope of the present inventive discovery.

Figure 1A:
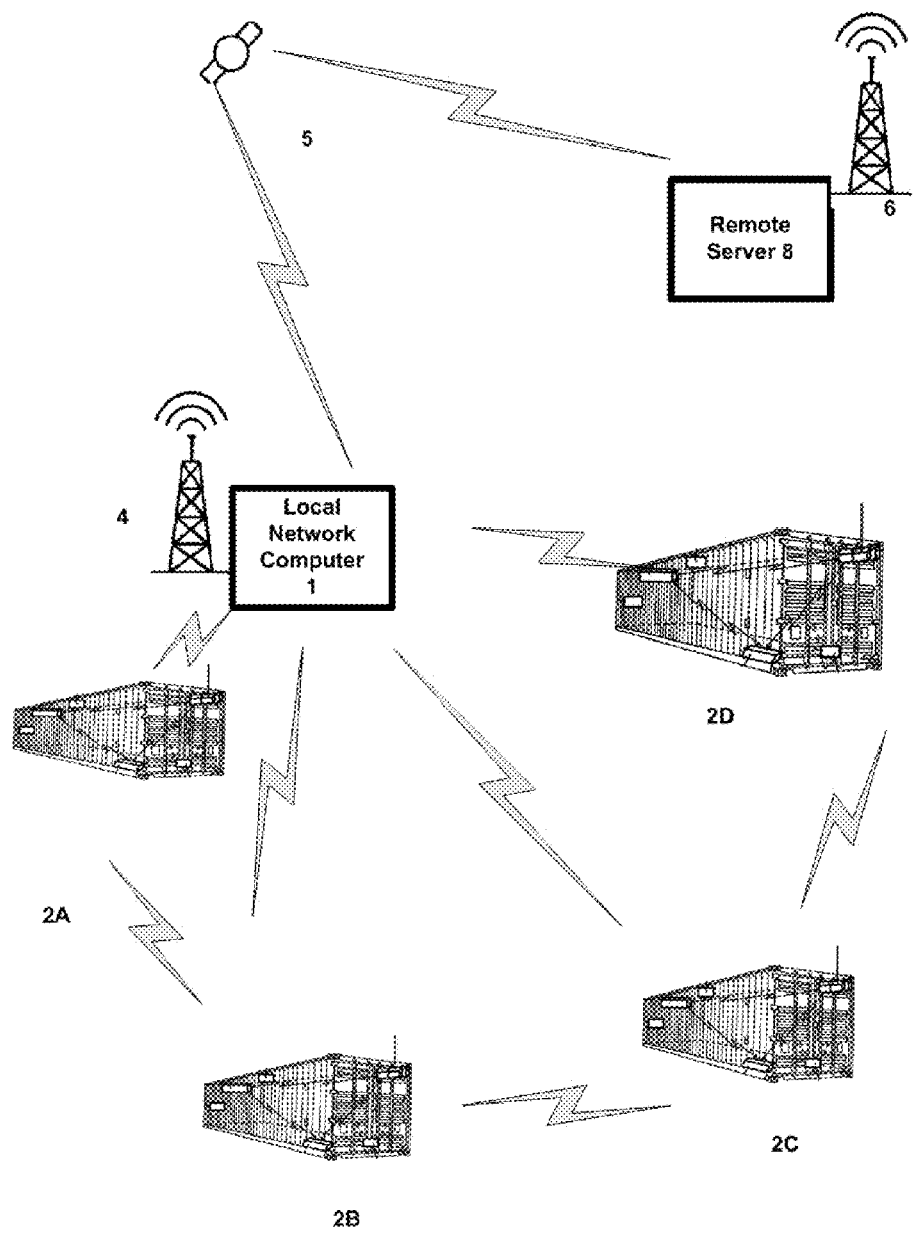
FIG. 1A shows a system for detecting in a shipping container the presence of explosives and other controlled substances such as drugs or narcotics as well as other chemicals used in clandestine activities.

FIG. 1A shows a system for the detection of explosives and other controlled substances such as drugs or narcotics as well as other chemicals used in clandestine activities in shipping containers 2A-2D. In FIG. 1A, each of shipping containers 2A-2D contains one or more detectors or testers such as those of FIG. 2. Within each of containers 2A-2D, the detectors can communicate with each other from node to node via a low power wireless mesh network such as ZigBee network, for example. The containers 2A-2D in turn consolidate data transmission and communicate with nearby containers, as well as a local network computer 1 which is local to a carrier of the containers. The carrier can be a transport unit for a shipping company, a railroad company, or an truck or airline based carrier such as Fedex or UPS, among others. The local network computer would periodically issue an instruction to perform a test for an explosive or a test for a drug, for example, and then polls each container for the result of the tests. The local network computer then transmits through an antenna 4 to a long range transceiver such as a cellular transceiver or to a satellite transceiver to a satellite 5, for example. The result of the transmission is received by a remote monitoring through a communication tower 8 center and a remote server 8 and suspicious cargo can be flagged for inspection.

The local computer 1 can communicate through cellular signals. In one embodiment, GPRS or EDGE cellular signals may be used to locate and track the shipping containers 2A-2D. GPRS is a non-voice service that allows information to be sent and received across a mobile telephone network. GPRS may supplement Circuit Switched Data (CSD) and Short Message Service (SMS). Alternatively, satellite signals such as those from Iridium satellite constellations can be used to link the local computer 1 and the remote server 8. Also, microsatellites can be used to facilitate the communication between the computer 1 and the server 8, among others.

The communication network may be used for communicating a record of manifest information to the remote monitoring center, the manifest information including a description of the shipping container contents; the destination; and the chemical composition of the content. The local network computer 1 or the remote server 8 may interrogate the testers with an RF signal, which may be received by, and/or may be incident upon, the detector. In response to the interrogation signal, the detector may transmit a response signal. The response signal from the testers may include, for example, an identification number, a location, and one or more chemical test results. Other information can be provided. For example the tester may provide information relating to the status of the test stripe, an environmental condition, such as, ambient temperature, humidity, among others. A tamper detection unit can be used to detect whether the container has been tampered with and to detect unauthorized opening of the shipping container.

Figure 1B:
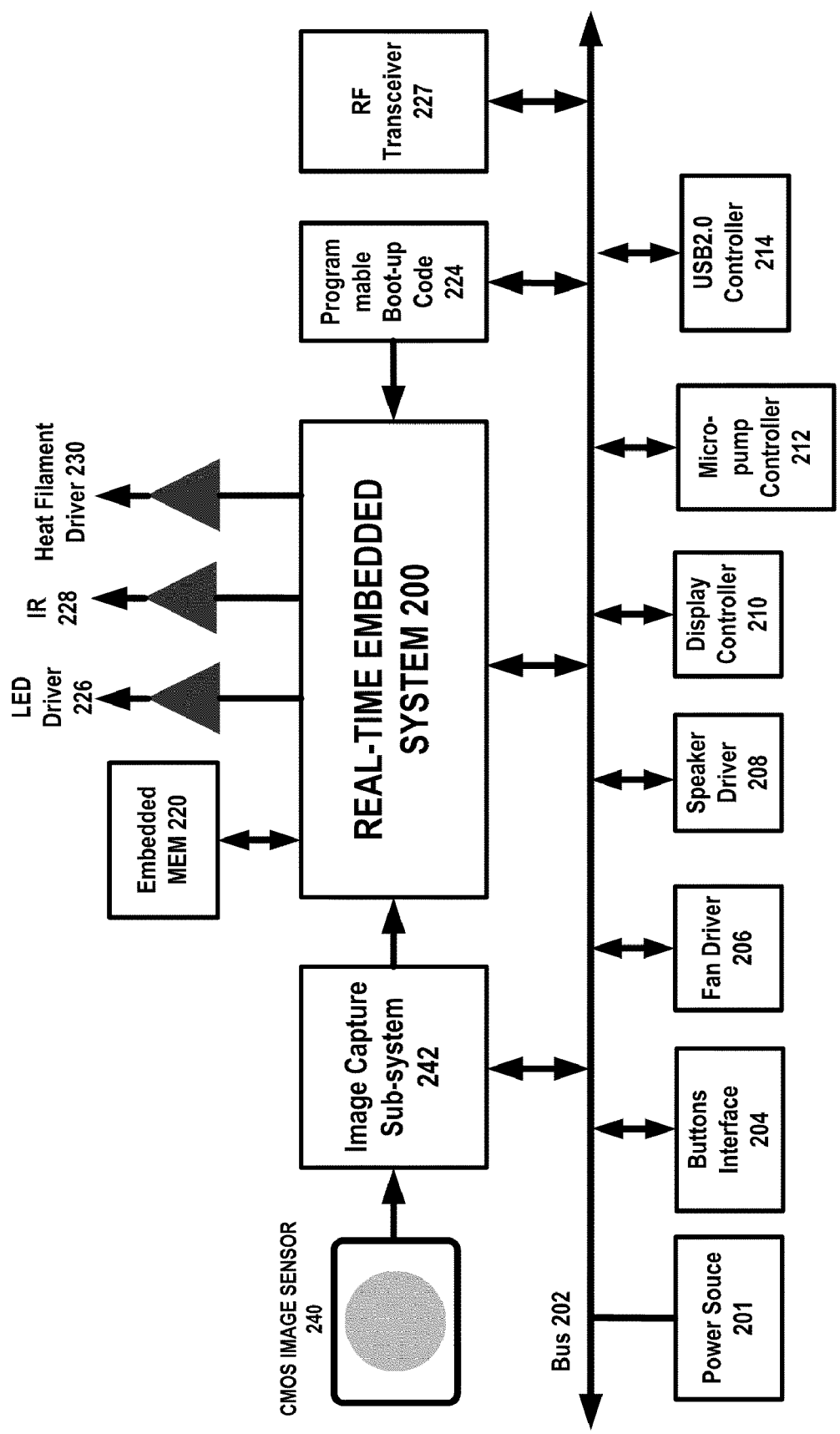
FIG. 1B shows an exemplary block diagram of processing electronics for detecting drugs or explosives.
Figure 2:
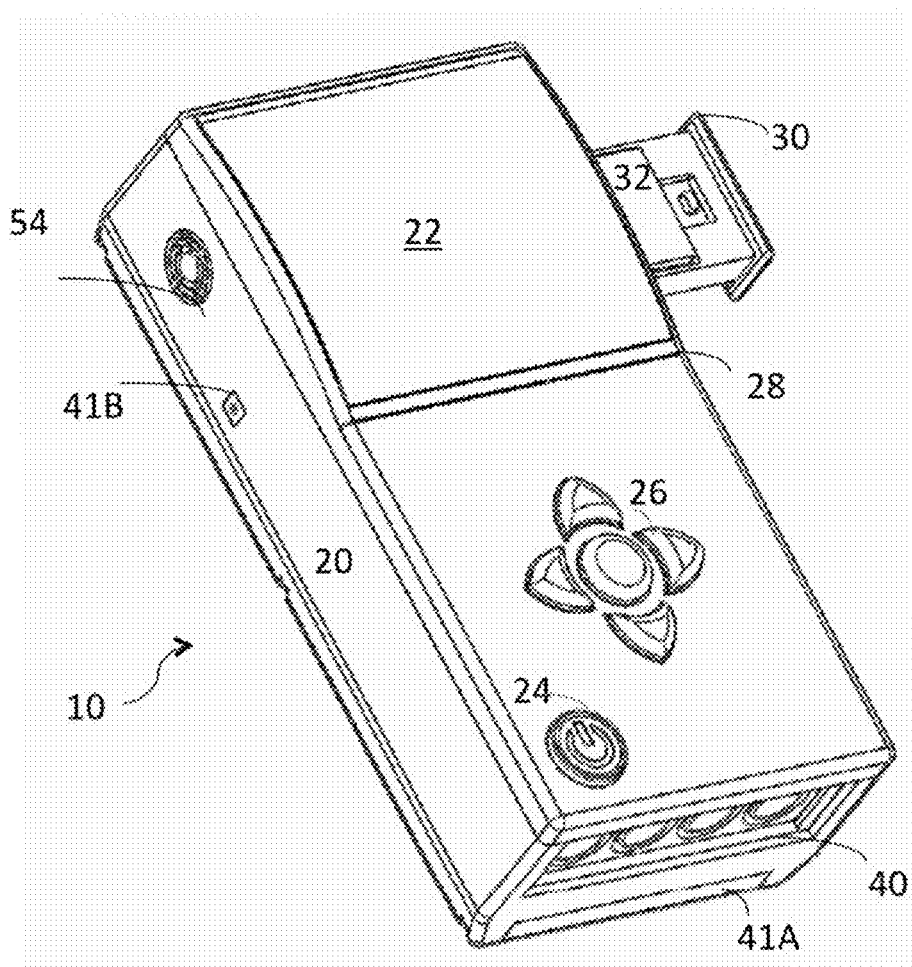
FIG. 2 shows an exemplary portable chemical detection device.

FIG. 1B shows an exemplary block diagram of processing electronics for the tester of FIG. 2. A processor 200 controls all tasks done by the system. The processor 200 communicates over a bus 202 to various devices, including buttons interface 204, fan driver 206, speaker driver 208, display controller 210, micro-pump driver 212, and USB controller 214. The processor 200 also communicates with embedded memory 220 and a programmable ROM 224 that contains boot code as well as application code. The processor 200 also drives buffers 227, 228 and 230 which controls the LED(s), infrared sensor that informs the operator if a swipe has been loaded into the test chamber 38, and heat filament, respectively. The infrared sensor is positioned under the swipe and acts as a proximity sensor to detect the presence or absence of a swipe by the amount of light reflected back. The processor 200 or controller actuates the motor to drive a solution delivery manifold to the center of the swipe and in close proximity to the swipe to dispense the solution without dripping, regardless orientation. The controller can monitor fluid levels within each reservoir contained in the disposable cartridge. This is done by decrementing available volume each time the pump is actuated and when the count reaches a low threshold, the controller can indicate that the reservoir is out of chemical.

A rechargeable power source 201 such as a battery can be used to power the camera and processor. The power source 201 can be charged by a vibrational energy scavenging charger such as the Volture Vibration energy harvester from Mide Technology Corp of Medford, Mass., for example. The Volture is a robust, reliable and inexpensive means to harvest vibration energy for the detector. The Volture vibration energy harvester device harvests otherwise wasted energy from mechanical vibrations of the carrier such as the train or ship vibrations. Piezoelectric materials convert mechanical strain into useable electrical energy. The piezoelectric materials are enclosed in a protective skin with pre-attached electrical leads, producing a highly reliable component with no soldered wires. The QuickPack actuator's protective skin also provides electrical insulation and defense against humidity and harsh contaminants.

The system can operate without rechargeability as well. The system is powered by a power source 201 such as a 12-volt DC source, which can be generated from an AC/DC converter, a car outlet or from eight 1.5-volt batteries in series. In one embodiment that does not use rechargeable power source, the highest prioritized energy source is from an AC/DC converter followed by the one from a container power outlet, then the energy from batteries. The 12-volt DC power source will supply current to the heater and the pump. It is also connected to the low drop voltage regulator to generate different voltage levels such as 5 V, 2.8 V and 3.3 V, which are necessary for the processor and for other peripherals as well.

The system has a radio-frequency transmitter/receiver (transceiver) 227 which can communicate with the local computer 1, or can send data through mesh networking by transmitting the data from container to container node until the data reaches its destination. The destination can be another container 2A, 2B, 2C, or 2D, or can be the local computer 1 for long range transmission to the local server 8.

In one embodiment, the transceiver 227 uses the WiFi (802.11) protocols. In another embodiment, the transceiver uses the ZigBee (802.15) protocols. The protocols automatically construct a low-speed ad-hoc network of nodes. In most large network instances, the network will be a cluster of clusters. It can also form a mesh or a single cluster. The current profiles derived from the ZigBee protocols support beacon and non-beacon enabled networks. In non-beacon-enabled networks (those whose beacon order is 15), an unslotted CSMA/CA channel access mechanism is used. In this type of network, ZigBee Routers typically have their receivers continuously active, requiring a more robust power supply. However, this allows for heterogeneous networks in which some devices receive continuously, while others only transmit when an external stimulus is detected. In the heterogeneous network, the ZigBee node that is connected to the mains supply is constantly on, while a battery-powered transponder would remain asleep until it is periodically wakened up to test for the presence of a target chemical. The transponder then sends a command to the mains powered transponder, receives an acknowledgment, and returns to sleep. In such a network the mains powered node will be a ZigBee Router, if not the ZigBee Coordinator; the battery powered node is a ZigBee End Device. In beacon-enabled networks, the special network nodes called ZigBee Routers transmit periodic beacons to confirm their presence to other network nodes. Nodes may sleep between beacons, thus lowering their duty cycle and extending their battery life.

In general, the ZigBee protocols minimize the time the radio is on so as to reduce power use. In beaconing networks, nodes only need to be active while a beacon is being transmitted. In non-beacon-enabled networks, power consumption is decidedly asymmetrical: some devices are always active, while others spend most of their time sleeping. The basic channel access mode is "carrier sense, multiple access/collision avoidance" (CSMA/CA). That is, the nodes talk in the same way that people converse; they briefly check to see that no one is talking before they start. There are three notable exceptions to the use of CSMA. Beacons are sent on a fixed timing schedule, and do not use CSMA. Message acknowledgments also do not use CSMA. Finally, devices in Beacon Oriented networks that have low latency real-time requirements may also use Guaranteed Time Slots (GTS), which by definition do not use CSMA.

The system of FIG. 1B can detect the presence of a predetermined substance by applying a sequence of chemicals onto the test swipe pad and taking an image of the result and performing image processing to detect changes on the test swipe pad. One example of the of a sequence involving chemistry time, temperature ramp rates and hold times to optimize each of the results for explosives, drugs, or other threat chemicals within a chemical reaction sequence. The system always adjusts the start temperature prior to running a particular sequence to a predetermined temperature value. An example of the temperature may be 35° C. where the swipe retaining a wet or dry sample is adequately held and in intimate contact with the elements of the swipe holder. The specific parameter controls for fan speed, LED lighting, pumping increments, GUI, camera, speaker, or display can be varied, as known to one skilled in the art.

The background image of the swipe at this temperature is taken so as to subtract out any colors that may be present on the swipe prior to analysis. A selected chemical reactant from one of the reservoirs is then pumped onto the swipe in a non-drip fashion and in a volume of 20-30 μL, most favorable being 25 μL. The system takes second image of the chemically reacted sample on the swipe and immediately processes this image from subtracted background for color indicating peroxides. The second image then becomes the new background image whether peroxides are present or not for the next analyte sought hexamethylene triperoxide diamine HMTD.

Further reacting sample material on the swipe, the heater element begins rapidly heating only the sample area on the swipe with temperature setting ramp rates of 10-20° C. per minute to 115° C., most favorable being 15° C. per minute. During the ramp, a third image is taken between 5-15 seconds, 12 seconds being most favorable, to analyze for color indicating HMTD. The system takes third image of the chemically reacted sample on the swipe and immediately processes this image from second background for presence of HMTD. Once the heater element reaches 115° C., it then holds a for 20-40 seconds, 30 seconds being most favorable. The third image then becomes the new background image whether HMTD was present or not for the next analyte sought triacetone triperoxide TATP.

During the hold time, a fourth image is taken of the chemically reacted sample on the swipe at 25 to 30 seconds, 28 seconds being most favorable, and immediately processes this image from third background for presence of the color indicating TATP. The fourth image then becomes the new background image whether TATP was present or not for the next analyte sought chlorates.

During the same hold time, a fifth image is taken of the chemically reacted sample on the swipe at 25 to 35 seconds, 30 seconds being most favorable, and immediately processes this image from fourth background for presence of the color indicating chlorates. The fifth image then becomes the new background image whether chlorates were present or not for the next analyte sought TNT.

The heater element begins rapidly heating only the sample area on the swipe with temperature setting ramp rates of 10-20° C. per minute to 140° C., most favorable being 15° C. per minute. Simultaneously, a second selected chemical reactant from one of the reservoirs is then pumped onto the swipe in a non-drip fashion and in a volume of 20-30 μL, most favorable being 25 μL. Once the heater element reaches 140° C., it then holds for 10-20 seconds, 10 seconds being most favorable. During the second temperature ramp, a sixth image is taken between 5-15 seconds, 8 seconds being most favorable, to analyze for color indicating TNT. The sixth image then becomes the new background image whether TNT was present or not for the next analytes sought all high explosives.

The heater element begins rapidly heating only the sample area on the swipe with temperature setting ramp rates of 10-20° C. per minute to 155° C., most favorable being 15° C. per minute. Simultaneously, a third selected chemical reactant from one of the reservoirs is then pumped onto the swipe in a non-drip fashion and in a volume of 20-30 μL, most favorable being 25 μL. Once the heater element reaches 155° C., it then holds for 10-20 seconds, 20 seconds being most favorable. During the third temperature ramp, a seventh image is taken between 5-15 seconds, 5 seconds being most favorable, to analyze for colors indicating all high explosives. The seventh image then becomes the new background image whether high explosives were present or not for the next analytes sought all nitrates.

The heater element continues to hold at 155° C. and from 10-20 seconds, an eighth image is taken between 10-20 seconds, 15 seconds being most favorable, to analyze for colors indicating all nitrates. The heater element immediately cools down for the next sample run.

Another example of a single test involving chemistry time, and temperature settings and hold times to optimize results for a chemical reaction involves depositing one or more of the chemical reactants from their respective reservoirs onto the swipe in a non-drip fashion. This is to impart a single spot test or multiple spot tests for a single drug or drugs, a single explosive or explosives, or other threat chemicals at ambient or preset temperature conditions that results in a single color or an array of colors unique to that material under the temperature settings and reagents applied.

The detection system of FIG. 1B significantly enhances the detection of the explosive materials. First, the device is pre-programmed and/or is remotely controlled to automatically rotate a swipes within the holder for intermittent and/or long term particle and/or vapor sampling by rotating a single swipe filter into position with connection to a pump or fan. A blank swipe filter on the opposite side of the holder may optionally be analyzed at the same time to provide a background level. Pumps or the automatically pumps a series of chemical solution agents into the swiped sample and heats up to specific temperature to accelerate the chemical reactions. Second, an internal CMOS camera captures the chemical reaction images at its highest resolution, raw data for better image analysis. Third it then sends these raw images data to the LCD (Liquid Crystal Display) screen for the purpose of observation. Moreover, the JPEG codec is capable storing and replaying image functions. The LCD screen provides a high quality image for human viewing. In another embodiment, in place of JPEG, a bitmap image or an MPEG video or any suitable imaging storage format can be used. The LCD can analyze the image to identify explosive materials based on the provided chemical reaction database. Last but not least, the PC interfaces can be used to update software and firmware as well as to backup the data.

In one implementation, to start the analysis process, the system turns the micro-pump(s) N (i.e., N=1, 2, 3 . . . or a combination thereof) to disperse the chemical solution into the Swiped Sample. The pumping rate is set to 2 Hz. After dispersing chemical solution, the system starts heating the sample to excite the chemical reactions under controlled vapor, time, temperature, and chemical volume conditions specific to a particular analyte or group of analytes. A current of about one ampere is applied to heat up the heating filament. During the heating process, the fluctuation of the temperature is controlled by a feedback circuit with a thermistor.

When the temperature of the sample swipe reaches a predefined value, the system turns the heater off, the white light LED on and the fan on. The speed of the fan is adjustable using pulse width modulation control in one embodiment.

Before commanding the camera's CMOS image sensor to capture an image, the system waits for the chemical reaction to complete for around 1 ms. The captured image is then displayed on the LCD.

The system creates a result image by subtracting the captured image from the background one. Then the result image is compared with the color patterns in the lookup table stored in the system. If the results image matches some color pattern, the result probability will be displayed and an optional audible alarm is given or not. Otherwise, an appropriate message is displayed on the LCD.

During the process of writing to the memory, (e.g., saving results or updating database), the system is able to detect the memory capacity and give the user a warning of full memory. In such a case, the user needs to clear the memory by deleting certain files before commanding the system to continue its work.

In one embodiment, the system executes a prime pump procedure to clear up air and chemical bubbles in the tubes of minimized length and diameter once the system has been idled for more than two weeks. If the system has not been used for the past two weeks then the system automatically rotates a swipe into position for automated priming of the pumps. During the prime pumps, the camera captures the image from the swipe and displays it on the LCD screen. During the prime pumps, no heat is applied to the swipe.

In one embodiment, in the main menu, before the unit is placed in the container, the user can see the date, the time and current status of the system. The system can generate a warning alarm once battery, chemical level and memory reach their minimal levels. The menu also contains three (3) software programmable buttons, namely New Analysis, Previous Results, and Settings. User can interact with these soft buttons by using the five hard buttons. The New Analysis option is highlighted as default. The usage of these soft buttons is as follows:

New Analysis: allows user to perform a new test.
Previous Results: allows user to trace back the data tested in the past.
Settings: allows user to set parameters such as date, time, to test the system reliability, or to connect to PC for firmware and/or database update.

The user can see the images taken by the camera. The system status is also displayed. In addition, three (3) soft buttons (Start, Stop, and Status) are provided for manual inspection if needed.

Each container tester can work with a user replaceable chemically treated pad, or can work with a swipe cartridge that is automatically advanced by a motor upon request. In a user replaceable pad arrangement, the container can only be tested once and the pad must be replaced before another test can be done. For example, if the container is opened at a port, before a ship goes through inspection, the container area is sealed off and an agent can go through each container and replace the pad at each point where third parties may have had access to the container and retest each container. For containers that need frequent testing, a motorized roll of chemically treated pad is provided and upon actuation, the roll can be advanced to expose the next chemically treated pad for testing.

In one embodiment, the chemically treated pad has a substantially round shape. A sequence of one or more chemicals can be delivered to the pad to detect an explosive compound. Each chemical or chemical sequence in tandem with temperature parameters over time causes the pad to display a color unique to the explosive compound. The sequence of chemicals are deposited onto the pad at predetermined times. The sequence of chemicals is deposited onto the pad at predetermined temperature range(s) achieved at a specific ramp rate. The sequence of chemicals is deposited onto the pad at predetermined hold time(s) each at predetermined temperature range(s). Each chemical deposited under predetermined time and temperature conditions reacts to a specific explosive or class of explosives to yield a specific color unique to that explosive. The chemically treated pad can be a substantially round shape of thickness less than 0.005 inches to achieve rapid, and even heating through the material layer, and adapted to receive a sequence of one or more chemicals to detect an explosive compounds. The base can have a non reflective dull black color. The pad region can be a cloth within a white zone on the base and an ink free border. The round swipe can be used for explosives in which a sequence of unique chemicals are deposited onto the same circular pad at specified times, temperature ramp rates, and hold times at a given temperature. Each chemical deposited under these time/temp conditions will react a specific explosive or class of explosives yielding a specific color unique to that explosive or class of explosives.

In another embodiment, a chemically treated pad can be a substantially four-sided shape with a plurality of test regions. A plurality of unique chemical solutions can be deposited on each test region. The chemical solutions can be deposited separately or at same time to the respective test regions on the swipe. One or more chemicals can be deposited onto the pad to detect one or more drug compounds. Each chemical causes the pad to display a color unique to the explosive compound or class of explosives. The colors generated on each pad, in combination, subsequently generate a color bar code unique to the drug or class of drugs. The sequence of chemicals are deposited onto the pad at predetermined times. The sequence of chemicals are deposited onto the pad at predetermined temperature range(s). The sequence of chemicals are deposited onto the pad at predetermined hold time(s) each at predetermined temperature range(s). Each chemical deposited under predetermined time and temperature conditions reacts to a specific explosive or class of explosives, drug or class of drugs to yield a specific color unique to that explosive or drug. The chemically treated pad can be a substantially four-sided shape of thickness less than 0.005 inches to achieve rapid and even heating through the material layer, and adapted to receive a sequence of one or more chemicals to detect a drug compound. Four different solutions can be deposited at same time to the respective rectangles on the swipe. The portable test device (FIG. 1B) will read the "color bar code" results to determine certain drugs. Then, the swipe will be heated through one to several heat ramp cycles to invoke more color changes to each of the respective rectangles creating new color bar codes. Each color bar code at a specific temperature and time will indicate a specific drug or clandestine material sought. A sampler/applicator can be used to sample a suspect material; in a baggie for example; and wipes the collected drug sample onto the square swipe pad.

The swipe pad may be formed of material that may be resistant to chemical degradation during testing in the approximate pH range of 0.1 through 14 to avoid reacting or decomposing. The swipe pad may be white in color to aid test evaluation, may be heat resistant and chemically resistant at elevated temperatures up to approximately 150° C. and may have hydrophilic properties for wetting only when using fluid reagents in the test apparatus. The swipe pad may also be roughened, for example, by use of a woven material, to aid in retrieving test sample particles from the environment. The swipe pad may also be thick enough to resist damage such as tearing during sampling, yet not be too thick such that heating of the test sample is inhibited. A thickness less than 0.005 inches to achieve rapid, and even heating through the material layer.

The test swipe can be used to swipe a sample to identify a chemical composition. This can be done by clamping the test swipe under a camera and above a heater, the test swipe having a base; a chemically treated pad containing the swiped sample positioned above the base in a white zone; and a tab attached to one side of the base; automatically pumping a series of chemical solution agents into the swiped sample without dripping so that the device may be held in any orientation; heating the swiped sample to one or more accurate predetermined temperatures and hold times to optimize and accelerate the chemical reactions; evacuation of vapors generated, capturing one or more images of the chemical reaction; sending the images to the a display screen for operator observation; and analyzing the images to identify the chemical composition based on a chemical reaction and sequence of occurrence and database.

The chemical solution agents are described next. A Tetrabutylammonium hydroxide formulation may be used in a reagent test to impart a color to nitroaromatic compounds that may otherwise not be detected by other bases, such as, sodium hydroxide or potassium hydroxide regardless of their respective concentrations. The tetrabutylammonium hydroxide may also be strong enough to create nitrite salts for other types of explosives that may be in the test sample in preparation for testing with a second type reagent. Use of tetrabutylammonium hydroxide may be difficult due to limited shelf life and its reaction to environmental carbon dioxide that may degrade the necessary color chemistry with nitroaromatics. To develop a solvent system mixable with water to inhibit degradation and reduce hazardous effects to a user, an ethanol and water mixture may be used to inhibit tetrabutylammonium hydroxide degradation with the ethanol ratio such as not to be flammable. The ethanol and water may also have minimum nitrite content to avoid reaction to a second type reagent test that may give false positive results. The tetrabutylammonium hydroxide may also be of a concentration in the ethanol water mixture so as not to interfere chemically with subsequent formulations added to the swipe. For example, if a 10 nanogram detection threshold may be used, any nitrite content in the solutions may be less than 0.2 nanograms per microliter of fluid to minimize corruption of test results or false detection.

The first reagent test may use a first reagent fluid that may have an optimum detection performance range with the fluid having a tetrabutylammonium hydroxide in a water solution in the approximate range of 65-850 percent and an ethanol as approximately 20-35 percent of the water solution. Test results may be obtained using a wider tolerance of elements in the first reagent fluid, but there may be reduced detection sensitively. The tetrabutylammonium hydroxide in water solution may be in the approximate range of 0.1 to 1.6 Molar and the ethanol as approximately 5 to 95 percent of the water solution. Also, other alcohols or blends of alcohols may be used in place of ethanol; however, for example, methanol may be toxic to the user and isopropyl may be less toxic, but may have poorer detection sensitivity results and cause shorter shelf life for the reagent fluid.

A second reagent test may be a Griess reagent test. The Griess reagent may cause a highly colored azo dye to be created in a reaction with nitrite salts generated from the first reaction or present as residue from firearms. The acid that may be used in the formulation of the second reagent may be phosphoric acid that reduces hazardous effects to a user that may become a buffer during the reaction thereby buffering against itself to inhibit creation of too much acid on the swipe pad. Other types of acids that may be used in the Griess test may react too violently with other bases, may be toxic or hazardous, or may create a strong odor.

The phosphoric acid may be mixed with sulfanilic acid and N-(1-naphthyl) ethylenediamine dihydrochloride. The sulfanilic acid may be water soluble with reduced toxicity in combination with and it may impart a deep magenta or fuchsia color to the test sample for ease of detection of explosives. N-(1-naphthyl)ethylenediamine dihydrochloride may be water soluble and not carcinogenic as with other salts, and may impart an effective color reaction from the test sample. The second reagent solution may use deionized water that may have minimum nitrite content to reduce false positive test results. For example, if a 10 nanogram detection threshold may be used any nitrite content in the solutions may be less than 0.2 nanograms per microliter of fluid to minimize corruption of test results or false detection.

The second reagent test may use a second reagent fluid that may have an optimum detection performance range with the fluid having a phosphoric acid in a water solution in the approximate range of 1.3 to 1.7 Molar; and a sulfanilic acid of approximately 8 grams with a N-(1-naphthyl)ethylenediamine dihydrochloride of approximately 5 grams per 1000 milliliters of the phosphoric acid in water solution. Test results may be obtained using a wider tolerance of elements in the second reagent fluid, but there may be reduced detection sensitivity. The phosphoric acid in water solution may be in the approximate range of 0.1 to 7.35 Molar, the sulfanilic acid may be in the approximate range of 5 to 8 grams, and the N-(1-naphthyl) ethylenediamine dihydrochloride may be in the approximate range of 5 to 9 grams. Other acids, acid combinations, or acid concentrations may be used, but may produce less than optimal testing sensitivity results. Other solutions may have increased acidity and be hazardous to the user as well as have a detrimental effect on the testing device. Other solutions may not be acidic enough for a detection reaction to occur or may be toxic. Other salts may be used, but they may reduce the explosives detection sensitivity.

FIG. 2 shows an exemplary portable chemical detection device 10 that uses the test swipes discussed above. The device 10 can be secured to the exterior of the shipping container, or can be placed inside the shipping container and suitably connected to an antenna that allows wireless communication to take place with the device 10. The device 10 has a housing 20 that supports an optional display 22 and input devices such as an on-off button 24 and navigation/selection buttons 26. In one embodiment, the system has six buttons.

The first button is the On/Off button. This button allows user to turn the unit on or off. The remaining five buttons (Left, Right, Down, Up, and Enter) allows a user to interact with a Graphical User Interface (GUI) of the system. The GUI is flexible, efficient and user friendly.

The device 10 also has an input/output port 28 such as a USB port or Firewire port to communicate with a remote computer, and AC power port, among others. In one embodiment, the I/O port 28 is a weather proof PC interface. The PC interface can set up operation parameters and recover analyzed data. In another embodiment, the I/O port 28 can include a flash memory card interface.

The device 10 also includes two ports 30 and 40 to receive user replaceable media and chemical. The device 10 also includes a port 41A to receive user replaceable DC battery cartridge. Port 30 receives a test swipe that is manually inserted by an operator in the embodiment of FIG. 2, although the present inventors contemplate that test swipes can be roll-mounted and moved to position through a motorized mount, for example. The port 40 receives a chemical cartridge, which can house one or more chemical containers. An electronic controller receives inputs from the buttons or keys and controls the display 22 and other electronics in the device 10. The system can work with different power sources including battery port 41A port and/or a DC input port 41B such as a 12V jack or an AC/DC adaptor.

To test a contaminate collection swipe, a user opens the port 30 and places a test swipe into a swipe holder. The swipe holder moves along sliding rails when the user closes the port 30 to place the test swipe under a test chamber. The test chamber includes a chamber with two openings that face a variable speed fan 54 to draw air across the test swab or test swipe while under test. The test chamber also includes a heating element 56 connected to a PID loop that can warm up the test swab to multiple predetermined temperature settings during test. The test chamber also contains a camera 39.

Figure 3:
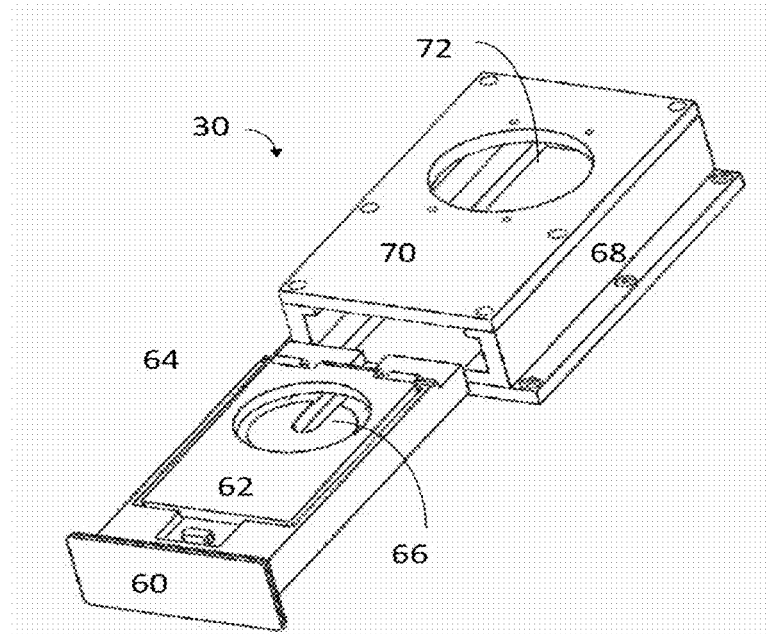
FIG. 3 shows in more details a swipe receiving port.

FIG. 3 shows in more detail port 30 that receives the test swipe in the swipe holder 64. The swipe holder 64 includes a door 60 by which a user can press against to open or close the port 30. The swipe holder 64 also includes an open face press-fit clamp 62 that secures the swipe against a heating element 64 under the swipe upon closure. The swipe holder 64 is attached to rails 66 that slide within rails 68 to enable the swipe holder 64 carrying the test swab to move in and out of the device 10. An enclosure for the swipe holder 64 is formed by positioning a lid 70 with an opening 72 between the sliding rails 68. The opening 72 allows movable tubes from the micro-pumps 46 to dispense test chemicals onto the swipe. The opening 72 also allows a camera 39 to capture images of the test results for automatic real-time analysis of the test. A white-light source such as one or more LEDs are positioned near the camera can be turned on to provide lighting if needed and turned off when not used to conserve power. In one embodiment, the camera output is shown on the display 22 so that the user or operator can visually determine the test result(s) while the automated determination is in progress. The opening 72 also allows a variable speed fan 54 to gently move vapor away from the camera lens to avoid fogging the lens (anti-fogging).

Figure 4:
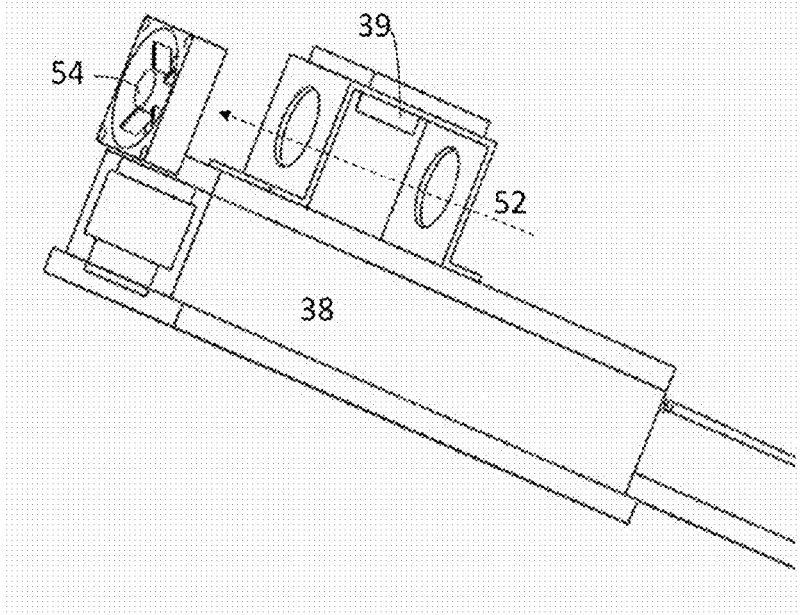
FIG. 4 shows an exemplary perspective view of a camera in a test chamber.

FIG. 4 shows an exemplary perspective view of a camera 39 in conjunction with the test chamber 38. The chamber 38 includes a motor driving a gear cooperating with a moveable arm that moves test tubing fixture back and forth over the test swab or swipe during testing. The test tubing fixture moves very closely to the swipe for chemical deposit onto the swipe when the device 10 is held in any orientation. The arm includes a plurality of piezoelectric pumps 46. The moveable arm also moves the fixture out of the way for the camera 39 to capture changes on the test swipe during testing. The camera images are then analyzed, and the result can then be displayed on the display 22. In one embodiment, the camera 39 can capture raw images with 65,536 colors. The camera is protected with an anti-fog feature using the adjustable speed fan 54. The image data can be shown continuously throughout the entire process on a flip-up display 22 with high fidelity. In one embodiment, the system provides a software JPEG (or alternatively bitmap) encoder and decoder for storing and viewing previous results and images. The system also includes white light LEDs (not shown) located within the test chamber 38 that provides even, shadow free, and uniform lighting during camera 39's operation with a programmable white light intensity. The LEDs minimize shadows in the camera viewing area.

The swipe holder 34 moves along rugged sliding rails 66 when the user closes the port 30 to place the test swipe under the test chamber 38. The test chamber 38 includes a chamber with two openings 52 that face the fan 54 to draw air across the test swipe while under test. The test chamber also includes a heating element 56 that can warm up the test swipe to a predetermined temperature during test.

Figure 5:
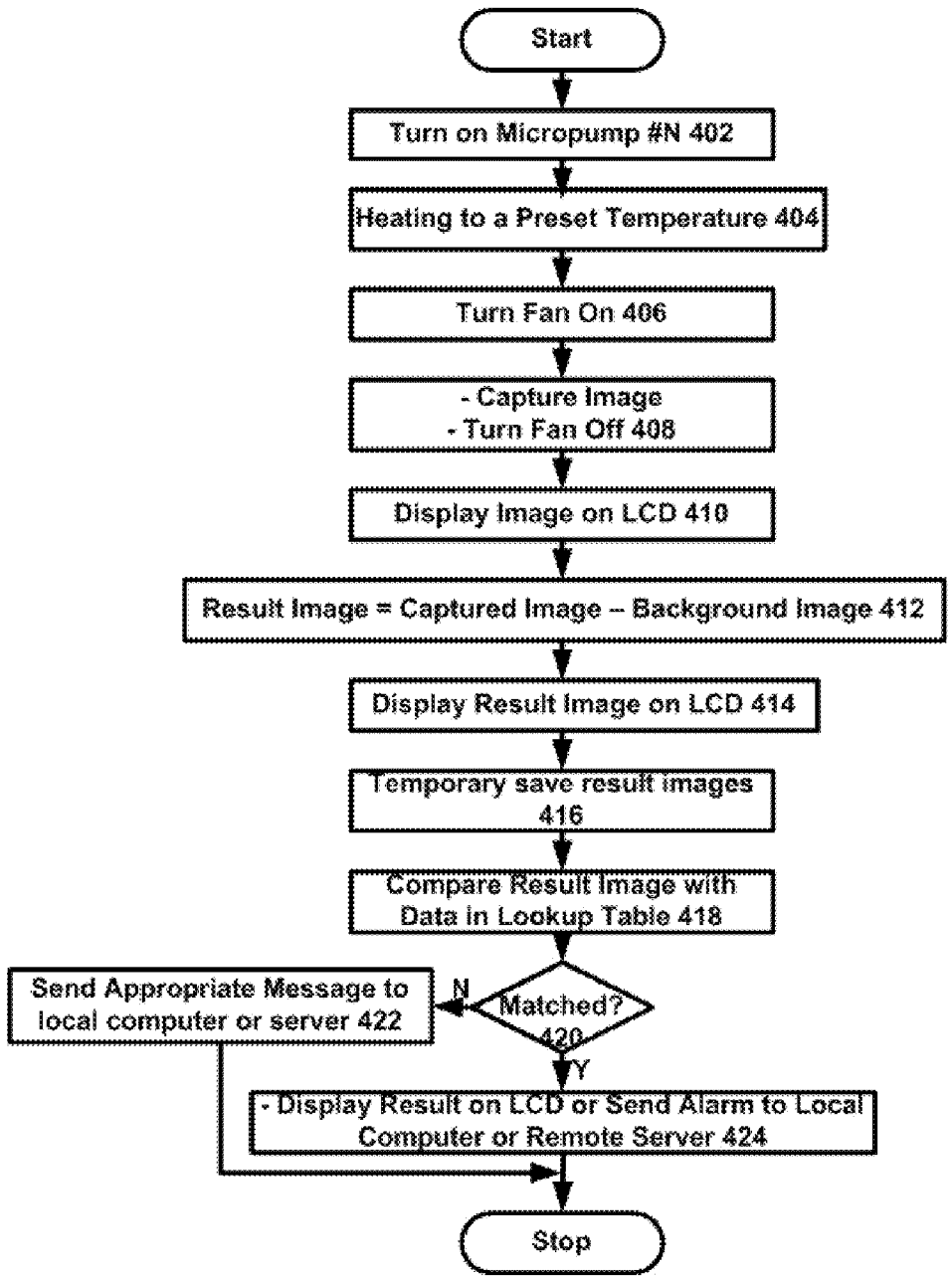
FIG. 5 shows an exemplary image analysis process executed by the system of FIG. 1B to test for the presence of a predetermined substance.

FIG. 5 shows an exemplary image analysis process executed by the real-time embedded system processor 200 to detect chemical agents automatically. To start the analysis process, the system turns the micro-pump(s) N (i.e., N=1, 2, 3 . . . or a combination thereof) to disperse the chemical solution into the swiped sample. The pumping rate is set to 0.250 Hz. After dispersing chemical solution, the system starts heating the sample to excite the chemical reactions. A current of about 1 Ampere is required to heat up the heater filament. When the temperature of the sample reaches a predefined value, the system turns the heater off, the LED and the fan on. In one embodiment, before commanding the CMOS image sensor to capture an image, the system waits for the chemical reaction to be optimized: time, temperature, volume dispensed, and vapor to complete for around 1 millisec. The captured image is then displayed on the LCD. The system creates a result image by subtracting the captured image from the background one. Then the result image is compared with the color patterns in the lookup table stored in the memory. If the results image matches some pattern, the result will be displayed and an alarm can be sent to the local computer 1 or the remote server 8, for example. Otherwise, if no dangerous substance has been detected, an appropriate message is sent to the computer or optionally displayed on the LCD.

Figure 6:
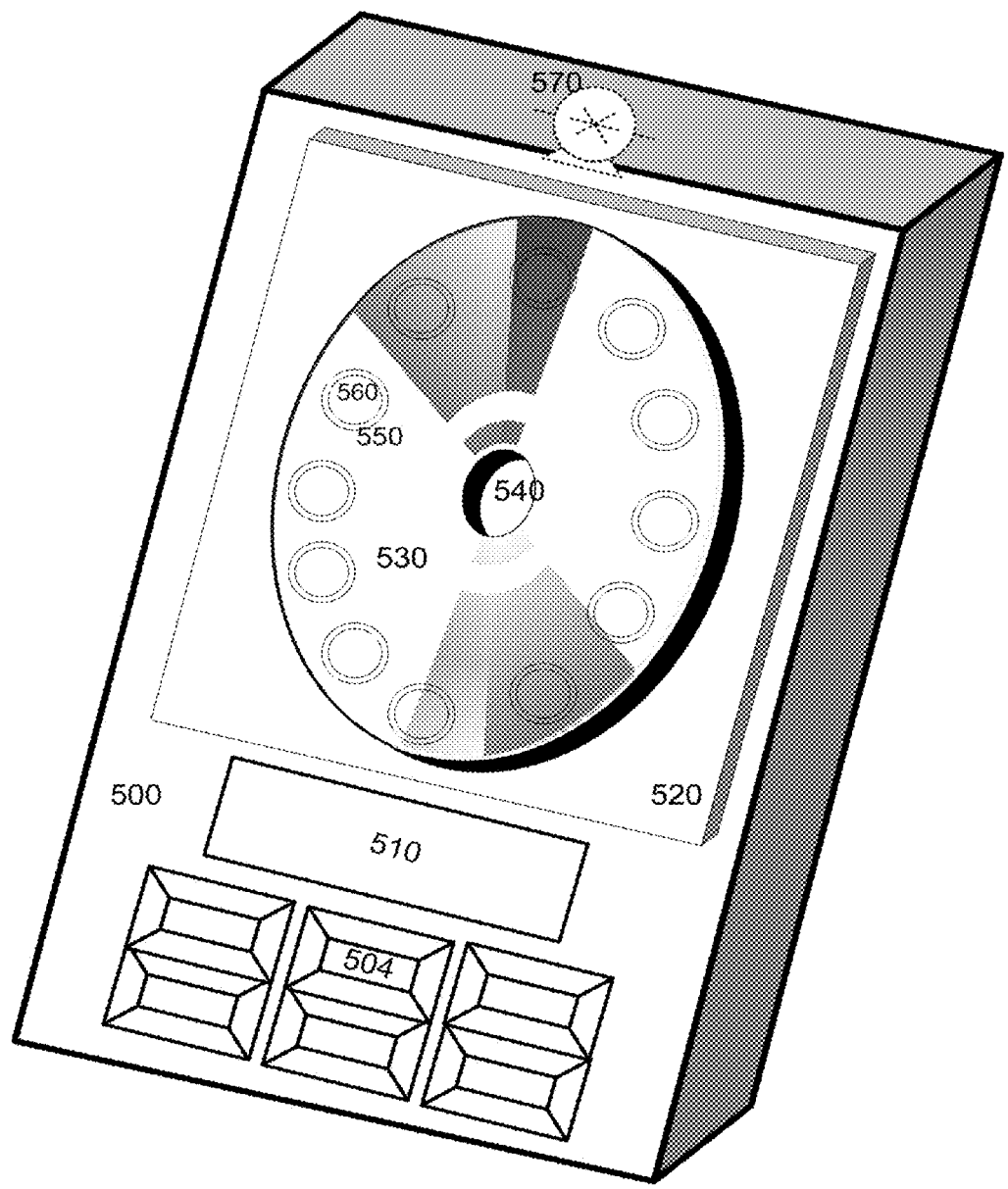
FIG. 6 shows an exemplary perspective of another embodiment of a shipping container tester.

FIG. 6 shows an exemplary perspective of another embodiment of a shipping container tester. In this embodiment, a tester 500 includes an exemplary user interface with a keypad 504 and a display 510. Using the keypad 504, the user can specify test parameters, enter current date/time, and heater parameter, among others. The display 510 can provide visual feedback, and in case of detection of a target chemical compound, the display can also display a warning. The tester 500 has a cover or lid 520 that provides a sealed environment for a test disc 530. The disc 530 includes a hub or an opening 540 that can be inserted into a rotating spindle of a motor (not shown). The motor can rotate to advance the disc 530 from one test position to another test position with a fresh test pad such as test pad 560. The test pad 560 is advanced to a position above a vacuum pump 570 inside the tester 500. The test pad 560 acts as a filter when the pump 570 is operated. During operation, a heater (not shown) is also activated to bring the temperature of the test pad 560 to a predetermined temperature or temperature range. In one embodiment, the disc 530 provides a heater guard 550 positioned between the pad 560 and the heater. In another embodiment, the heater guard 550 is positioned on a second disc that is rotated into position prior to heating and pumping operations. As in the other embodiments, a chemical solution dispensing system such as a micropump is used to dispense chemicals from one or more chemical reservoirs into the test pad 550. Also, the test pad can be made from a material to receive one or more chemical dispensing operations, or alternatively can have a plurality of test strips each receiving different test chemicals thereon.

The chemical dispenser can be located on one side or on both sides of the disc, they move together on the same assembly. The dispensers are not directly opposite each other in an effort to prevent interaction between test operations on each of the two media surfaces. In one embodiment, a very small spindle motor engages the metal hub at the center of the disc 530. A stepper motor can be used to make a precise number of stepped revolutions to move the chemical dispenser to the proper track position. The chemical dispenser assembly is fastened to the stepper motor shaft.

A system of levers can be used to open the lid 520 to allow the user to exchange the disc 530. Alternatively, the lid 520 can be eliminated by using an external button that allows the disc to be in a slot and to be ejected when desired.

During operation of the dual disc embodiment, the motor first rotates the disc with the swipe or test pad 560 to the air filter position above the pump 570 and then moves the disc with heater guard between the test pad 560 and the heater. The system then prepares the test pad 560 (such as warming up the test pad 560). The system then moves the chemical dispenser into place above the test pad 560 and applies the chemical solution(s) and then heat is applied. After dispensing one or more chemical solutions onto the test pad 560 for the chemical threat analysis and controlling the temperature of the pad 560, the vacuum pump 570 is operated to remove vapors that can fog up a predetermined distance from the pad 560. After a predetermined period, a camera (not shown) is used to capture images of the test pad 560 and image processing operations are done to detect the absence or presence of a particular chemical compound. The system waits for the chemical reaction to be optimized: time, temperature, volume dispensed, and vapor to complete for around 1 millisecond in one embodiment. The captured image is then displayed on the LCD display 510. The system creates a result image by subtracting the captured image from the background one. Then the result image is compared with the color patterns in the lookup table stored in the memory. If the results image matches some pattern, the result will be displayed and an alarm can be sent to the local computer 1 or the remote server 8, for example. Otherwise, if no dangerous substance has been detected, an appropriate message is sent to the computer or optionally displayed on the display 510.

In one embodiment, the system can remotely and automatically collect sample particles by air filtration on a series of swipes at under remote control or any pre-set, predetermined time. The system can analyze any or all swipes on command to identify a chemical composition collected according to date and time. In one embodiment, the system includes a series of pre-loaded swipes in a cartridge whereby the test swipes are clamped in the holder, rotated in and out of a air filtration position for any period of time controlled by the operator, and the test swipes may then be rotated under a camera and above a heater. The test swipe can have a base; a chemically treated pad containing the swiped sample positioned above the base; and a tab attached to one side of the base. The system can actuate a piezoelectric transducer or pumps that deposits a series of chemical solution agents into the swiped sample without dripping so that the device may be held at any angle of position or orientation; heating the swiped sample to one or more predetermined temperatures at a controlled rate and hold times to optimize and accelerate the chemical reactions. The system then captures one or more images of the chemical reaction; sends the images to the a display screen for operator observation; and analyzes the images to identify the chemical composition based on a chemical reaction and sequence of occurrence and database.

Due to the automated, reproducible analysis, the system provides an objective indication of potential threats with more accurate, un-biased results at night, high humidity, or bad weather conditions, and therefore, more convenient.

The invention may be implemented in hardware, firmware or software, or a combination of the three. Preferably the invention is implemented in a computer program executed on a programmable computer having a processor, a data storage system, volatile and non-volatile memory and/or storage elements, at least one input device and at least one output device.

By way of example, a block diagram of a computer to support the system is discussed next. The computer preferably includes a processor, random access memory (RAM), a program memory (preferably a writable read-only memory (ROM) such as a flash ROM) and an input/output (I/O) controller coupled by a CPU bus. The computer may optionally include a hard drive controller which is coupled to a hard disk and CPU bus. Hard disk may be used for storing application programs, such as the present invention, and data. Alternatively, application programs may be stored in RAM or ROM. I/O controller is coupled by means of an I/O bus to an I/O interface. I/O interface receives and transmits data in analog or digital form over communication links such as a serial link, local area network, wireless link, and parallel link. Optionally, a display, a keyboard and a pointing device (mouse) may also be connected to I/O bus. Alternatively, separate connections (separate buses) may be used for I/O interface, display, keyboard and pointing device. Programmable processing system may be preprogrammed or it may be programmed (and reprogrammed) by downloading a program from another source (e.g., a floppy disk, CD-ROM, or another computer).

Each computer program is tangibly stored in a machine-readable, removable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

The invention has been described herein in considerable detail in order to comply with the patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A portable chemical analytical apparatus, comprising:
a shipping container;
a housing adapted to be mounted on or in the shipping container;
a chemical reservoir insertable into the housing;
a plurality of disposable test swipes for sequential dispensing, wherein each disposable test swipe is sequentially dispensed by an actuator in a disc or an automated cartridge, each test swipe upon contact with one or more chemicals in concert with heating and time profiles, displays a sequence of a plurality of color reactions unique to multiple analytes, including explosives, drugs, or household chemicals;
a programmable thin-film heater to accurately heat and hold the disposable test swipe to a plurality of predetermined temperatures each at a predetermined hold time and then return to a start temperature;
a clamp to uniformly secure the disposable test swipe to the thin-film heater;
one or more pumps programmed to automatically dispense repeatable and accurate volumes on one or more chemicals from a disposable cartridge onto the disposable test swipe in concert with heating and time profiles to evoke a sequence of a plurality of color reactions unique to predetermined multiple analytes, including explosives, drugs, or household chemicals;
a programmable fan to remove chemical vapors rising a predetermined distance from the test swipe but leaving vapors immediately in contact with the swipe; and
an automated programmable camera and optics system to automatically and uniformly light and capture a sequence of multiple images of color changes occurring over heat, chemical reaction and time profiles on the test swipe for an immediate automated analysis to specifically and uniquely identify an analyte of interest from the predetermined multiple analytes and for real-time viewing on a display screen by an operator providing a secondary level of assessment.

2. The apparatus of claim 1, comprising a processor to perform a color analysis of specific hue pixels uniquely appearing from the analyte of interest under controlled heat, controlled time, and chemical reaction sequences in real-time and to store data according to positive or negative identification and detection of the analyte of interest.

3. The apparatus of claim 1, comprising a processor coupled to each pump to dispense chemical solutions in predetermined sequences.

4. The apparatus of claim 1, comprising a processor coupled to a heater that heats up the disposable test swipe sample to predetermined temperatures and hold time sequences using an automatic ramped heating feedback control providing results unique to the analytes sought.

5. The apparatus of claim 1, a processor coupled to a fan, wherein the fan provides the camera and optics system with anti-fog protection in predetermined fan sequences.

6. The apparatus of claim 1, wherein the camera output is shown real time on the display during the sample run.

7. The apparatus of claim 1, comprising a JPEG encoder and decoder for storing and viewing previous results and images.

8. The apparatus of claim 1, comprising a processor coupled to a programmable light emitting diode (LED) array to provide uniform lighting for the camera imaging of the sample area on the disposable test swipe in predetermined sequences.

9. The apparatus of claim 1, comprising a processor to perform automatic calibration under different lighting and temperature environments.

10. The apparatus of claim 1, comprising a processor coupled to the one or more pumps to dispense micro volumes of one or more solutions on the disposable test swipe in a predetermined sequence.

11. The apparatus of claim 1, comprising a processor coupled to a proximity sensor to detect the presence of a swipe.

12. The apparatus of claim 11, wherein the proximity sensor comprises an infrared sensor or snap switch.

13. The apparatus of claim 1, comprising a processor controlled motor to drive a solution delivery manifold to the center of a test area on the disposable swipe and in close proximity to the swipe to dispense a solution without dripping, regardless of orientation.

14. The apparatus of claim 1, comprising a processor controlled sensor to monitor fluid levels within each chemical reactant reservoir contained in the disposable cartridge.

15. The apparatus of claim 1, wherein the sequence of chemicals are deposited onto the pad at predetermined hold time(s) each at predetermined temperature range(s).

16. The apparatus of claim 1, comprising a plurality of test swipes positioned near the disc perimeter.

17. The apparatus of claim 1, comprising a motor to rotate the disc.

18. The apparatus of claim 1, comprising a heater guard positioned between the test swipe and a heater.

19. The apparatus of claim 18, wherein the heater guard is positioned on a second disc.

20. A method to analyze a shipping container for chemical signatures, comprising:
mounting on or in the shipping container a plurality of disposable test swipes for sequential dispensing by an actuator in a disc or an automated cartridge, each test swipe upon contact with one or more chemicals in concert with heating and time profiles, displays a sequence of a plurality of color reactions unique to multiple analytes, including explosives, drugs, or household chemicals;
clamping the disposable test swipe to a thin-film heater that uniformly heats a predetermined test area on the test swipe in a test chamber;
controlling the heater to expose the test swipe through predetermined timed temperature sequences;
dispensing one or more chemicals from a manifold assembly in timed sequences onto the predetermined test area on the disposable swipe through one or more pumps drawing from one or more reservoirs in the disposable cartridge throughout a predetermined temperature profile and time sequence;
removing chemical vapors rising a predetermined distance from the test swipe but leaving vapors immediately in contact with the swipe; and
capturing a sequence of colors evolving specific to each analyte on the test area of the disposable swipe for differentiating, detecting, and identifying specifically one of a plurality explosives by taking a series of images, at specific heat and times in the sequence of chemical reactions on the test area of the swipe for analysis.

* * * * *